(12) United States Patent
Imaji et al.

(10) Patent No.: US 10,967,115 B2
(45) Date of Patent: Apr. 6, 2021

(54) TOXIN SEPARATOR

(71) Applicant: Kureha Corporation, Tokyo (JP)

(72) Inventors: Makoto Imaji, Tokyo (JP); Kaori Kikuchi, Tokyo (JP); Yoshiharu Itoh, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 16/969,590

(22) PCT Filed: Jan. 10, 2019

(86) PCT No.: PCT/JP2019/000595
§ 371 (c)(1),
(2) Date: Aug. 13, 2020

(87) PCT Pub. No.: WO2019/167441
PCT Pub. Date: Sep. 6, 2019

(65) Prior Publication Data
US 2021/0001034 A1  Jan. 7, 2021

(30) Foreign Application Priority Data

Mar. 1, 2018  (JP) .............................. JP2018-036930

(51) Int. Cl.
*A61M 1/36*  (2006.01)
*B01J 20/28*  (2006.01)
(Continued)

(52) U.S. Cl.
CPC ........ *A61M 1/3679* (2013.01); *A61M 1/3417* (2014.02); *B01D 15/38* (2013.01); *B01J 20/20* (2013.01); *B01J 20/2808* (2013.01); *B01J 20/28019* (2013.01); *B01J 20/28059* (2013.01); *B01J 20/28071* (2013.01);
(Continued)

(58) Field of Classification Search
CPC .............. A61M 1/3417; A61M 1/3679; A61M 2202/0498; B01J 20/20; B01J 20/28059; B01J 20/2808; B01J 20/28083; B01J 20/28085; B01J 20/28019; B01J 20/28071; B01D 15/38
See application file for complete search history.

(56) References Cited

U.S. PATENT DOCUMENTS

2017/0252370 A1  9/2017  Honda et al.

FOREIGN PATENT DOCUMENTS

JP   2004-256324 A   9/2004
JP   2008-303193 A   12/2008
(Continued)

OTHER PUBLICATIONS

International Preliminary Report on Patentability (Chapter II) of the International Preliminary Examining Authority for PCT/JP2019/000595 with search date of Mar. 4, 2020.
(Continued)

*Primary Examiner* — John Kim
(74) *Attorney, Agent, or Firm* — Thomas F. Quinn, Jr.

(57) ABSTRACT

Provided are a toxin separator and the like which are capable of selectively separating toxin present in a biological fluid by binding to protein, from the toxin and the protein. The toxin separator of the present invention also includes activated carbon of which a pore volume of pores having a pore diameter from 1.4 to 35 nm as measured by a nitrogen adsorption method is 0.06 cm$^3$/g or greater.

7 Claims, 3 Drawing Sheets

(51) Int. Cl.
    *A61M 1/34*          (2006.01)
    *B01J 20/20*         (2006.01)
    *B01D 15/38*        (2006.01)

(52) U.S. Cl.
    CPC ... *B01J 20/28083* (2013.01); *B01J 20/28085* (2013.01); *A61M 2202/0498* (2013.01)

(56) References Cited

FOREIGN PATENT DOCUMENTS

| | | |
|---|---|---|
| JP | 2016-117650 A | 6/2016 |
| WO | 2016/031908 A1 | 3/2016 |

OTHER PUBLICATIONS

English translation of International Preliminary Report on Patentability (Chapter II) of the International Preliminary Examining Authority for PCT/JP2019/000595 with search date of Mar. 4, 2020.
International Search Report of the International Searching Authority for PCT/JP2019/000595 dated Mar. 19, 2019.
English translation of International Search Report of the International Searching Authority for PCT/JP2019/000595 dated Mar. 19, 2019.
Written Opinion of the International Searching Authority of PCT/JP2019/000595 dated Mar. 19, 2019.
English translation of Written Opinion of the International Searching Authority of PCT/JP2019/000595 dated Mar. 19, 2019.

TOXIN SEPARATOR

TECHNICAL FIELD

The present invention relates to a toxin separator that separates toxin from a biological fluid.

BACKGROUND ART

In order to remove toxins contained in blood of a patient with renal disease, a method has been performed to form a blood circulation path outside the body of the patient, remove the patient's blood out of the body, perform a purification treatment outside the body, and then return blood back into the body of the patient. A porous separation membrane such as a polysulfone dialysis membrane has been utilized in the related art as a representative means for such blood purification. A specific example is a hollow fiber type dialyzer in which a housing is filled with a hollow fiber membrane (porous separation membrane) made of polysulfone. In a common hollow fiber type dialyzer, blood flows inside the hollow fiber and a dialysate flows outside the hollow fiber. In the porous separation membrane in the related art, a pore size is adjusted to remove low molecular weight toxins such as urea and creatine by filtration and diffusion from the blood side to the dialysate side, but not allow blood cells, platelets, necessary proteins for body, such as albumin, and complement in blood to pass through. As such, a solute having a relatively high molecular weight is difficult to be removed from the blood.

Therefore, a method of using activated carbon to remove relatively high molecular weight toxins is known. For example, Patent Document 1 discloses a spherical activated carbon for direct hemoperfusion of which a diameter is from 0.1 to 1 mm, H/C is 0.14 or less, and a pore volume of the pores having a pore diameter from 5 to 1000 nm is from 0.25 to 0.55 mL/g. The adsorption ability of this spherical activated carbon for direct hemoperfusion for toxic substances having a molecular weight from approximately 100 to 1000 is at least as high as that of the spherical activated carbon in the related art, but it is described that the adsorption ability for the toxic substances having a molecular weight from approximately 1000 to 10000 is further improved than that of the spherical activated carbon in the related art.

On the other hand, there is also a toxin bound to the protein in the blood. For example, indoxyl sulfate, which is toxin, is known to be significantly accumulated by binding to albumin (molecular weight of approximately 66000) in the blood of a patient with renal disease. Furthermore, it is also reported that indoxyl sulfate is involved in various pathologies (such as pruritus and cardiovascular diseases) of a patient with renal disease (in particular, a hemodialysis patient). However, the toxins bound to these proteins can hardly be removed with dialysis using the porous separation membrane in the related art. Therefore, as a solution to reduce the accumulation of indoxyl sulfate, there is a method in which indole, a precursor of indoxyl sulfate, is adsorbed in a digestive tract using an oral adsorbent including spherical activated carbon, and thereby the production of indoxyl sulfate is suppressed. For example, Patent Document 2 discloses an adsorbent for oral administration including spherical activated carbon having a ratio of (pore volume of pores having a pore diameter of less than 3 nm)/(pore volume of pores having a pore diameter from 3 to 50 nm) of 3.0 or greater as an adsorbent for oral administration capable of adsorbing a large amount of indole.

CITATION LIST

Patent Document

Patent Document 1: JP 2004-256324 A
Patent Document 2: WO 2016/031908

SUMMARY OF INVENTION

Technical Problem

However, in Patent Document 1, the toxin bound to the protein is not mentioned as an adsorbed target. In addition, in the spherical activated carbon disclosed in Patent Document 1, there is a risk that the protein is removed along with the toxin.

For an oral adsorbent including spherical activated carbon as disclosed in Patent Document 2, toxins such as indoxyl sulfate already present in the blood cannot be reduced by direct adsorption. In addition, the use for the dialysis patient is practically off-label, and the present situation is that it is limited to use for the patient with chronic renal failure in the preservation period for the purpose of delaying introduction into hemodialysis.

Therefore, an object of one embodiment of the present invention is to provide a toxin separator which is capable of selectively separating toxin present in a biological fluid by binding to protein from the toxin and the protein.

Solution to Problem

In order to solve the problem described above, according to one embodiment of the present invention, there is provided a toxin separator that separates toxin from a biological fluid, wherein the toxin is bound to protein to be present in the biological fluid, and the toxin separator includes activated carbon having a pore volume of pores having a pore diameter from 1.4 to 35 nm, as measured by a nitrogen adsorption method of 0.06 cm$^3$/g or greater.

According to one embodiment of the present invention, there is provided a blood purification system including the toxin separator and a dialyzer.

According to one embodiment of the present invention, there is provided a toxin separation method of separating toxin from a biological fluid, wherein the toxin is bound to protein to be present in the biological fluid, and the method includes passing the biological fluid through the toxin separator.

According to one embodiment of the present invention, there is provided an activated carbon for toxin separation that separates toxin from a biological fluid, wherein the toxin is bound to protein to be present in the biological fluid, and the activated carbon has a pore volume of pores having a pore diameter from 1.4 to 35 nm, as measured by a nitrogen adsorption method, of 0.06 cm$^3$/g or greater.

Advantageous Effects of Invention

According to one embodiment of the present invention, toxin present in a biological fluid by binding to protein can be selectively separated from the toxin and the protein. Therefore, harmful toxicity can be efficiently removed from the biological fluid while leaving necessary proteins for body in the biological fluid.

DESCRIPTION OF EMBODIMENTS

An embodiment of the present invention will be described below. In the present specification, "to" is used to mean that the numerical values described therebefore and thereafter are included as the lower limit value and the upper limit value.

[1. Toxin Separator]

According to one embodiment of the present invention, there is provided a toxin separator that separates toxin from a biological fluid, wherein the toxin is bound to protein to be present in the biological fluid, and the toxin separator includes activated carbon having a pore volume of pores having a pore diameter from 1.4 to 35 nm, as measured by a nitrogen adsorption method, of 0.06 cm$^3$/g or greater.

(Biological Fluid)

In the present specification, the liquid obtained from the living body refers to a biological fluid. Examples of the biological fluid include a body fluid such as blood, plasma, serum, urine and ascites, and a cell culture fluid. The biological fluid may be untreated or may be subjected to any treatment. In one example, the biological fluid is blood obtained from a patient in need of hemodialysis. The origin organism is not particularly limited, and examples thereof include mammals, birds, reptiles, and the like, preferably mammals including pets such as dogs and cats; domestic animals such as cows, horses, and pigs; and humans.

(Toxin)

A toxin separated by the toxin separator according to one embodiment of the present invention is a toxin (protein-bound toxin) that is bound to protein to be present in the biological fluid. Examples of such a toxin include a uremic toxin. Examples of a protein-bound uremic toxin include a uremic toxin having a low molecular weight (molecular weight less than 500) such as indoxyl sulfate, 3-carboxy-4-methyl-5-propyl-2-furanpropionic acid (CMPF), hippuric acid, homocysteine, indole-3-acetic acid, N-carboxymethyl lysine, p-cresyl sulfate, pentosidine, phenylsulfate, quinolinic acid, spermidine, and glyoxal. In one example, the molecular weight of the toxin can be 58 or greater and less than 500.

Note that, there is no need that 100% of toxin is bound to the protein in the biological fluid, and at least a portion (for example, 10% or greater, 20% or greater, 30% or greater, 40% or greater, 50% or greater, 60% or greater, 70% or greater, 80% or greater, 90% or greater, 95% or greater, or 99% or greater) may be bound.

Examples of the protein to which the toxin is bound include albumin, and a1-acidic sugar protein. In one example, the protein is a biologically necessary proteins for body. The molecular weight of the protein can be, for example, 10000 or greater, 30000 or greater, or 60000 or greater.

The toxin separator according to one embodiment separates the toxin from the biological fluid for one or more types of protein-bound toxins.

(Activated Carbon)

The toxin separator according to one embodiment of the present invention includes activated carbon of which a pore volume (mesopore volume) of pores (in the present specification, referred to as "mesopores") having a pore diameter from 1.4 to 35 nm, as measured by a nitrogen adsorption method, is 0.06 cm$^3$/g or greater. The mesopore volume is preferably 0.08 cm$^3$/g or greater, more preferably 0.10 cm$^3$/g or greater, and still more preferably 0.12 cm$^3$/g or greater. An upper limit of the mesopore volume is not particularly limited, and from the viewpoint of strength, the volume is preferably 1.0 cm$^3$/g or less, and more preferably 0.80 cm$^3$/g or less. A specific method of measuring mesopore volume by the nitrogen adsorption method is as described in the examples described below.

The inventors of the present application have been found, as described in examples described below, that the pore volume (micropore volume) of pores (in the present specification, referred to as "micropores") having a pore diameter from 0.5 to 1.4 nm and the pore volume (macropore volume) of pores (in this specification, referred to as "macropores") having a pore diameter from 50 to 10000 nm are not correlated with an adsorption rate of the toxin to be separated, and only the mesopores are correlated with the adsorption rate of the toxin to be separated. Note that, in the present specification, the micropore volume is measured by a carbon dioxide adsorption method, and the macropore volume is measured by a mercury intrusion porosimetry. These specific methods are as in the examples described below.

The toxin separator according to the present embodiment separates the toxin from the biological fluid by the action of activated carbon. Specifically, the activated carbon selectively adsorbs toxin from the toxin and the protein. Thus, the protein is left in the biological fluid. The adsorption rate of the protein is lower than the adsorption rate of the toxin, and in one example, the adsorption rate of the protein is less than 1%, and preferably 0%.

The activated carbon preferably has a pore (macropore) surface area of 0.10 m$^2$/g or greater having a pore diameter from 50 to 10000 nm as measured by a mercury intrusion porosimetry. In this case, the adsorption speed (in particular, the initial adsorption speed) of the toxin is increased. The macropore surface area is more preferably 0.25 m$^2$/g or greater, and still more preferably 0.40 m$^2$/g or greater. A specific method of measuring macropore surface area by the mercury intrusion porosimetry is as in the examples described below.

A bulk density of the activated carbon is not particularly limited, and is preferably 0.30 g/cm$^3$ or greater and more preferably 0.40 g/cm$^3$ or greater from the viewpoint of a crushing force. From the viewpoint of the adsorption properties, the density is preferably 0.70 g/cm$^3$ or less, and more preferably 0.60 g/cm$^3$ or less. Furthermore, in this specification, the bulk density is a value obtained by dividing the dry weight W (g) of the activated carbon when the activated carbon is filled in a container by the volume V (cm$^3$) of the filled activated carbon.

The crushing force of the activated carbon is not particularly limited, and from the viewpoint of reducing the generation of fine powders, the crushing strength is preferably 100 g/particle or greater, and more preferably 200 g/particle or greater. In the present specification, the crushing force of the activated carbon can be measured according to the examples described below.

The crushing strength of the activated carbon is not particularly limited, and from the viewpoint of reducing the generation of fine powders, the crushing strength is preferably 2.0 kg/mm$^3$ or greater, and more preferably 3.5 kg/mm$^3$ or greater. In the present specification, the crushing strength of the activated carbon can be measured according to the examples described below.

The shape of the activated carbon is not particularly limited, and examples thereof include a spherical shape, a fibrous shape, a powdery shape, and a granulated material. The shape of the activated carbon is preferably a spherical shape. In the case of the spherical shape, a contact area between the activated carbons is small, so that the biological fluid easily passes between the activated carbon. Further, since the structure has no corners, chipping is less likely to occur, and fine powders are less likely to be generated, and thereby clogging can be reduced. As a result, the biological fluid easily passes, and safety is also enhanced.

In the case where the activated carbon is spherical, the average particle size is not particularly limited, and from the viewpoint of pressure loss, the average particle size is preferably 100 μm or greater, more preferably 200 μm or greater, and still more preferably 250 μm or greater. From the viewpoint of the adsorption speed, it is preferably 1500 μm or less, more preferably 800 μm or less, and still more preferably 600 μm or less. In this specification, an average particle size means the particle size at a cumulative particle size percentage of 50% on a volume based cumulative particle size distribution curve ($D_{v50}$).

From the viewpoint of suppressing the generation of fine powders and ensuring the safety, it is preferable to use activated carbon that is produced as a lump rather than powdery activated carbon that is granulated with a binder or the like.

The activated carbon can use any carbon-containing material as a carbon source. Examples of the carbon-containing material include a synthetic resin and a pitch. As the synthetic resin, both a heat fusible resin (thermosetting resin) and a heat infusible resin (thermoplastic resin) can be used. Examples of the pitch include a petroleum pitch and a coal pitch. Furthermore, the activated carbon that is a raw material of a plant may be used, and examples thereof include wood, charcoal, rice husks, palm shells, and palm shells. From the viewpoint of the low amount of impurities, a synthetic resin or pitch is preferable.

The activated carbon can be produced, for example, according to the examples described below.

The toxin separator includes the activated carbon. In one embodiment, the toxin separator is a column. The amount of the activated carbon in the column is not particularly limited, and may be selected as appropriate depending on the type of the biological fluid, the amount of the biological fluid, the shape of the activated carbon, and the like. In one embodiment, the toxin separator is a blood purification column, and the amount of activated carbon is preferably from 50 to 500 g/column, preferably from 75 to 400 g/column, and more preferably from 100 to 300 g/column.

In addition, the size of the housing of the column is not particularly limited, and may be appropriately selected depending on the purpose.

In another embodiment, the toxin separator is a filter. The size of the filter is not particularly limited, and may be selected as appropriate depending on the type of the biological fluid, the amount of the biological fluid, the shape of the activated carbon, and the like.

[2. Blood Purification System]

Figure 1:
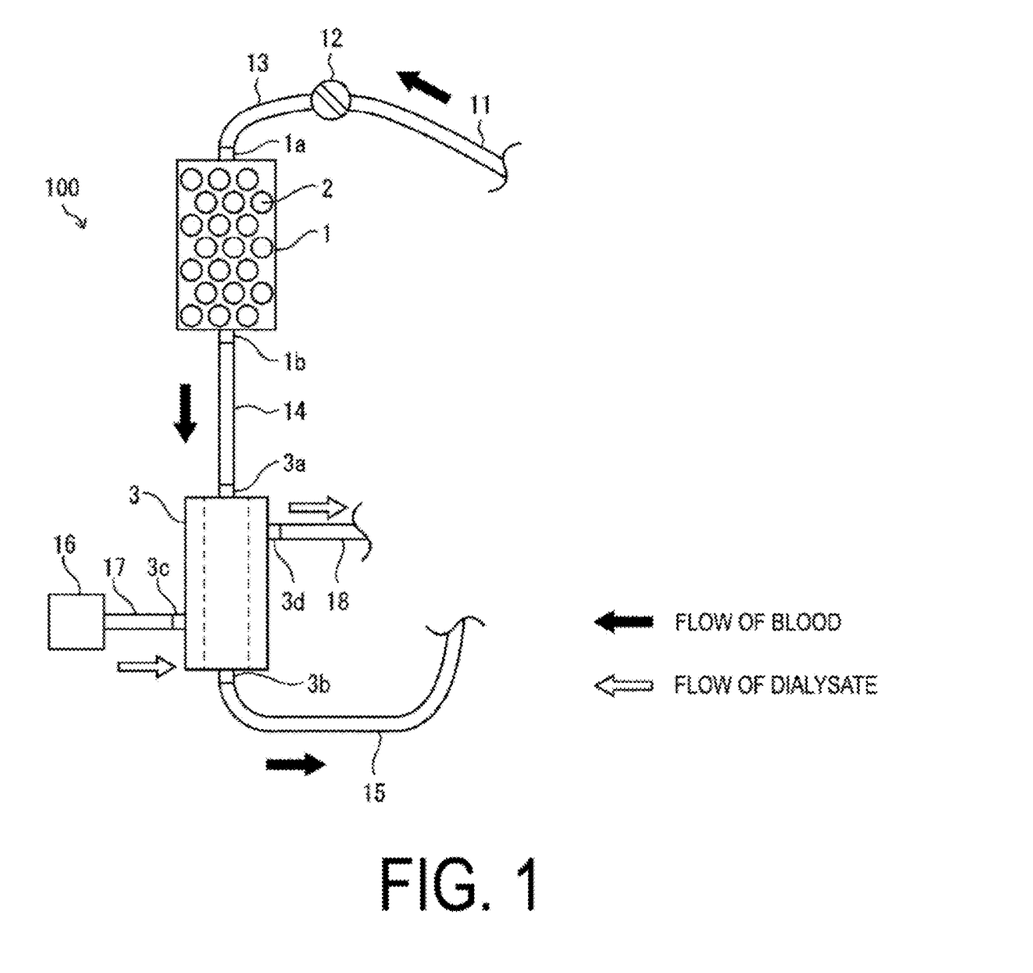
FIG. 1 is a schematic diagram illustrating an example of a blood purification system according to one embodiment of the present invention.

A blood purification system according to one embodiment of the present invention includes the toxin separator described above and a dialyzer. Hereinafter, the blood purification system will be described with reference to FIG. 1. FIG. 1 is a schematic diagram illustrating an example of a blood purification system 100 according to one embodiment of the present invention.

As shown in FIG. 1, the blood purification system 100 includes at least a toxin separator 1 and a dialyzer 3.

The toxin separator 1 is a column (blood purification column) including a large proportion of activated carbon 2 therein. The toxin separator 1 includes a blood inlet 1a for inflowing blood and a blood outlet 1b for outflowing purified blood.

The dialyzer 3 is an existing dialyzer (for example, a hollow fiber type dialyzer). In the dialyzer 3, a pore size of the porous separation membrane is adjusted to remove low molecular weight toxins such as urea and creatine by filtration and diffusion from the blood side to the dialysate side, but not allow proteins such as blood cells, platelets, albumin, and complement in blood to pass therethrough. The dialyzer 3 includes a blood inlet 3a for inflowing blood and a blood outlet 3b for outflowing purified blood. In addition, the dialyzer 3 includes a dialysate inlet 3c for inflowing dialysate and a dialysate outlet 3d for outflowing dialysate. The dialysate inlet 3c is connected to a dialysate supply unit 16 (for example, with a dialysate supply device and a dialysis monitoring device) via a tube 17. A tube 18 is connected to the dialysate outlet 3d. At the time of use, the dialysate flows from the dialysate supply unit 16 in the order of the tube 17, the dialyzer 3, and the tube 18, and is discarded in a dialysate recovery unit (not illustrated, may be the dialysis monitoring device, for example) or the like downstream of the tube 18.

In the blood purification system 100, the toxin separator 1 is disposed upstream of the dialyzer 3, and the blood outlet 1b of the toxin separator 1 and the blood inlet 3a of the dialyzer 3 are connected via a tube 14. Thus, blood having passed through the toxin separator 1 is configured to flow into the dialyzer 3.

A tube 13 is connected to the blood inlet 1a of the toxin separator 1. Furthermore, a pump 12 for pumping blood is connected to the tube 13. Furthermore, a tube 11 is connected to the pump 12. The tube 11 is inserted into a blood vessel of a dialysis patient at the time of using the blood purification system 100.

A tube 15 is connected to the blood outlet 3b of the dialyzer 3. The tube 15 is inserted into a blood vessel of a dialysis patient at the time of using the blood purification system 100.

That is, the blood purification system 100 is one in which the toxin separator 1 is further disposed in front of (upstream of) the dialyzer 3 in a typical hemodialysis configuration in the related art.

Note that, since the description of the configuration is simplified, other members may be inserted at any position. In addition, the blood purification system 100 is configured to include at least the toxin separator 1 and the dialyzer 3, but other members (such as the members described above, for example) can optionally be included in the blood purification system 100.

In use of the blood purification system 100, the blood flows from the dialysis patient in the order of tube 11, the pump 12, the tube 13, the toxin separator 1, the tube 14, the dialyzer 3, and the tube 15, and then returns to the dialysis patient.

In other embodiments, the toxin separator 1 may be disposed downstream of the dialyzer 3.

Note that, in the specification of the present invention, "purification" means that at least a part of toxins of at least one type (one or more types) of protein-bound toxins in the biological fluid is separated from the biological fluid. In one embodiment, 40% or greater, preferably 70% or greater, and more preferably 90% or greater of the toxin of at least one (one or more types) of the protein-bound toxin in the biological fluid is separated from the biological fluid.

[3. Toxin Separation Method]

A toxin separation method according to one embodiment of the present invention is a method of separating toxin from a biological fluid, wherein the toxin is bound to protein to be present in the biological fluid, and the method includes passing the biological fluid through the toxin separator. The description of the biological fluid, the toxin, the protein, and the like is as described in [1. Toxin separator].

Figure 2:
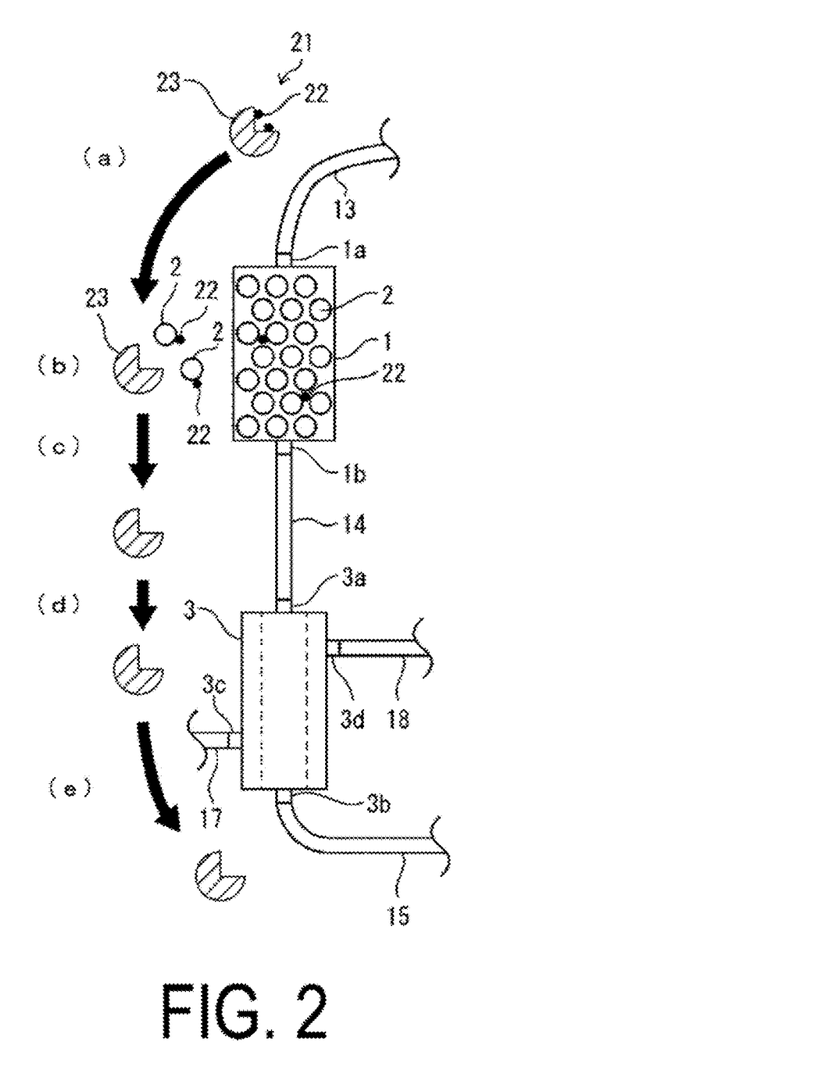
FIG. 2 is a schematic diagram illustrating separation of protein-bound toxin during use of the blood purification system according to one embodiment of the present invention.

As an example of the toxin separation method, a method including passing blood through the toxin separator 1 will be described with reference to FIG. 2. FIG. 2 is a schematic diagram illustrating separation of the protein-bound toxin during use of the blood purification system 100.

(a) First, blood (biological fluid) from the dialysis patient flows from the blood inlet 1a into the toxin separator 1. In the blood, there is a toxin-protein complex 21 in which a protein-bound toxin 22 (for example, a protein-bound uremic toxin) is bound to protein 23.

(b) The blood flowing into the toxin separator 1 contacts the activated carbon 2 in the toxin separator 1. At this time, the specific mechanism is not particularly limited, but the activated carbon 2 adsorbs the toxin 22 in the toxin-protein complex 21. On the other hand, the activated carbon 2 does not adsorb proteins 23.

(c) The blood then flows out from the blood outlet 1b. In the blood flowing out from the blood outlet 1b, the amount of the toxin 22 decreases by the amount adsorbed by the activated carbon 2. In this way, by passing blood through the toxin separator 1, the toxin 22 bound to the protein 23 to be present in the blood can be separated from the blood.

(d) In addition, blood flowing out from the toxin separator 1 passes through the dialyzer 3 to perform the dialysis in the related art. This removes other toxins. At this time, the protein 23 in the blood is not removed by the dialyzer 3 as described above.

(e) Therefore, the protein 23 such as albumin remains in the blood flowing out from the dialyzer 3.

As described above, according to the blood purification system 100, the removal amount of the toxin 22 that is bound to the protein 23 to be present in the blood is dramatically increased as compared with the case (that is, the configuration using only the dialyzer 3) in the related art. A plurality of types of toxins 22 may be separated by the toxin separator 1. Also, the toxin (non-protein-bound toxin) that is not bound to protein may also be separated by the toxin separator 1.

Note that, in the toxin separation method, the aforementioned (d) and (e) are optional. In one embodiment, the toxin separation method further includes passing the biological fluid through the dialyzer before or after passing the biological fluid through the toxin separator described above.

In addition, since the biological fluid is purified by this toxin separation method, the "toxin separation method" can also be referred to as a "biological fluid purification method".

The toxin separator according to the present embodiment is used outside the body, and therefore the toxin separation method is performed outside the body.

[4. Activated Carbon for Toxin Separation]

According to one embodiment of the present invention, there is provided an activated carbon for toxin separation that separates toxin from a biological fluid, wherein the toxin is bound to protein to be present in the biological fluid, and the activated carbon has a pore volume of pores having a pore diameter from 1.4 to 35 nm, as measured by a nitrogen adsorption method, of 0.06 $cm^3/g$ or greater.

The description of the biological fluid, the toxin, the protein, and the like, and specific descriptions of the activated carbon are as described in [1. Toxin separator].

[5. Others]

The present invention also provides a dialysis method using the toxin separator described above or the blood purification system as described above.

The present invention also provides a method of treating or preventing uremia using the toxin separator described above or the blood purification system as described above. In this method, in particular, uremia caused by a protein-bound uremic toxin is treated or prevented.

The present invention also provides activated carbon of which a pore volume of pores having a pore diameter from 1.4 to 35 nm as measured by a nitrogen adsorption method is 0.06 $cm^3/g$ or greater.

The present invention also provides a column filler for filling a column separating toxin from the biological fluid, wherein the toxin is bound to protein to be present in the biological fluid, and the filler contains activated carbon of which a pore volume of pores having a pore diameter from 1.4 to 35 nm, as measured by a nitrogen adsorption method, is 0.06 $cm^3/g$ or greater.

Embodiments of the present invention will be described in further detail hereinafter using examples. The present invention is not limited to the examples below, and it goes without saying that various aspects are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents described in the present specification are herein incorporated by reference.

EXAMPLES

<Various Measurement Methods>

[Average Particle Size]

A particle size accumulation curve was produced in accordance with JIS K 1474 for spherical activated carbon. For the average particle size, in the particle size accumulation curve, a horizontal line is drawn on a horizontal axis from an intersection of a vertical line at 50% point on the horizontal axis and the particle size accumulation line, and a sieve opening (mm) indicated by the intersection is obtained and set as the average particle size.

[Bulk Density]

After filling a graduated cylinder with activated carbon, tapping was repeated until the volume did not change. A dry weight W (g) of the activated carbon at this time was divided by a volume V ($cm^3$) of the activated carbon, and the bulk density was calculated.

[Crushing Force]

A force was applied to one spherical activated carbon particle sandwiched between sieves having the same size as the average particle size, and the force when the spherical activated carbon was broken was measured at N=30, and the average thereof was set as the crushing force.

[Crushing Strength]

The crushing strength was calculated by dividing the crushing force by the volume calculated from the average particle size.

[Specific Surface Area]

The specific surface area (SSA) was measured in accordance with the method stipulated in JIS Z8830. That is, the gas adsorption quantity of activated carbon can be measured using a specific surface area analyzer that uses the gas adsorption method (for example, ASAP2010 available from Micromeritics Corp.), and a specific surface area can be calculated using the equation below. Specifically, a sample tube was filled with the activated carbon sample, and after vacuum-drying at 300° C., post-drying sample weight was measured. Then, the sample tube was cooled to −196° C. and nitrogen was introduced into the sample tube to adsorb nitrogen on the spherical activated carbon sample, and the relationship between nitrogen partial pressure and adsorbed quantity (adsorption isotherm) was measured.

A BET plot is created, with the relative pressure of nitrogen taken as p and the adsorbed quantity at that time taken as v (cm$^3$/g STP). Specifically, the range of p from 0.02 to 0.20 was plotted with p/(v(1−p)) on the vertical axis and p on the horizontal axis, and the specific surface area S (units: m$^2$/g) was determined by the following equation from the slope b (units: g/cm$^3$) and intercept c (units: g/cm$^3$) at that time.

$$S = \frac{MA \times (6.02 \times 10^{23})}{22414 \times 10^{18} \times (b+c)} \quad \text{(Equation 1)}$$

Here, MA was a nitrogen atom cross-sectional area, and 0.162 nm$^2$ was substituted.

[Micropore Volume]

It was measured using "Autosorb (registered trademark)-iQ" available from Quantachrome Instruments. First, a sample tube was filled with a sample, and vacuum heat drying was performed at 200° C. for 12 hours to remove impurities such as moisture in pores of the sample. Then, a sample temperature was lowered to −78° C. by using dry ice ethanol under reduced pressure. Here, the carbon dioxide pressure was changed and introduced stepwise, and the adsorption amount of carbon dioxide of the sample at each pressure was measured. From the relationship between the obtained pressure and the adsorption amount of carbon dioxide, the volume (cm$^3$/g) of pores having a pore diameter from 0.4 to 1.5 nm was measured using the delocalized density functional theory (NLDFT).

[Mesopore Volume]

The mesopore volume was measured using "Autosorb (registered trademark)-iQ" available from Quantachrome Instruments. First, a sample tube was filled with a sample, and vacuum heat drying was performed at 200° C. for 12 hours to remove impurities such as moisture in pores of the sample. Then, a sample temperature was lowered to −196° C. by using liquid nitrogen under reduced pressure. Here, the nitrogen pressure was changed and introduced stepwise, and the adsorption amount of nitrogen of the sample at each pressure was measured. From the relationship between the obtained pressure and the adsorption amount of nitrogen, the volume (cm$^3$/g) of pores having a pore diameter from 1.5 to 35 nm was measured using a Barrett Joyner Hallenda method.

[Macropore Volume]

The macropore volume was measured using a mercury porosimeter (for example, AUTOPOREIV 9500 available from Micromeritics Corp.). First, a sample was put in a sample container, and degassed for 30 minutes under a pressure of 2.67 Pa or lower. Then, mercury was intruded into the sample container, pressure was gradually increased penetrate the mercury (maximum pressure: 414 MPa). From the relationship between pressure and mercury penetration quantity at this time, the pore volume distribution was measured using the calculation equation below. Specifically, the volume of mercury that penetrates the sample is measured from a pressure equivalent to pore diameter 89 μm (0.01 MPa) to the maximum pressure (414 MPa, equivalent to pore diameter 3 nm). In the calculation of pore diameter, when mercury penetrates into the pores of a cylinder having a diameter (D) at a pressure (P), and the surface tension of mercury is taken as "γ" and the contact angle between mercury and the pore wall is taken as "θ," the following equation holds true: −πDγ cos θ=π(D/2)2·P Therefore, D=(−4γ cos θ)/P.

In the present specification, the surface tension of mercury is taken as 484 dyne/cm and the contact angle between mercury and carbon is taken as 130 degrees. When the pressure P is expressed in MPa and the pore diameter D is expressed in μm, the relationship between the pressure P and the pore diameter D is determined by using the following equation: D=1.27/P.

For example, the pore volume in the range of pore diameter of 50 nm to 300 nm is equivalent to the volume of mercury that penetrates at mercury penetration pressure from 4.2 MPa to 25.4 MPa.

[Macropore Surface Area]

Assuming that the shape of the pores is cylindrical, the volume is V=πD$^2$L/4 and a side surface area A=πDL, which can be represented by D=4V/A. Assuming that a volume increase dV in one measurement section (pore diameter section) is due to cylindrical pores having one average pore diameter, the specific surface area increased in that section is determined as dA=4 dV/Dav (Day is an average pore diameter). The pore surface area was determined by calculating an integrated specific surface area ΣA at an average pore diameter from 50 to 10000 nm.

[Pressure Loss]

Pressure loss (transmission resistance) was measured when a fluid passed through the activated carbon sample. A mini-module was created by filling a container having an inlet for inflowing a fluid and an outlet for outflowing the fluid (for example, "Mobicol polypropylene column" available from Mobitec) with 200 mg of activated carbon sample. Water was passed using a peristaltic pump, a pressure (P1) on the inlet side of the mini module and a pressure (P2) on the outlet side of the mini module were measured, and the pressure drop (ΔP=P1−P2) before and after the mini module was calculated.

[Amount of Fine Powders Generated]

Water was added to the activated carbon sample, the adhered dust was sieved by ultrasonic cleaning, the suspension was filtered through a membrane filter, and the weight increase after drying was set as the amount of carbon dust. Specifically, first, 5.0 g of the activated carbon sample was placed in a 100 mL Erlenmeyer flask and weighed to 0.1 mg with a precision chemical balance. 100 mL of pure water was added to the Erlenmeyer flask, the mixture was placed in an ultrasonic cleaner for 3 minutes, and the suspension was filtered through a sieve with a mesh opening of 105 μm to separate the suspension filtrate and activated carbon. On the other hand, the membrane filter was dried at 110° C. for 1 hour, then cooled in a desiccator and weighed to 0.1 mg on a precision analytical balance. The membrane filter thus weighed was set in a Millipore filter suction device, and the suspension filtrate was filtered. The activated carbon remaining on the sieve was returned to the Erlenmeyer flask, 100 mL of tap water was added, and the operations of ultrasonic cleaning and separation of the suspension filtrate and activated carbon were repeated three times in total.

The membrane filter after filtration was dried at 110° C. for 1 hour, then cooled in a desiccator for 30 minutes, and weighed to 0.1 mg on a precision analytical balance. The carbon dust amount (D) is calculated by the following equation:

$$D\ (ppm)=[(B-A)/S]\times 10^6$$

In the above equation, A is the mass (g) of the membrane filter before the first filtration, B is the mass (g) of the membrane filter after the third filtration, and S is the mass (g) of the activated carbon sample firstly charged into the Erlenmeyer flask.

[Adsorption Test 1 (Immersion Method)]

An indoxyl sulfate and albumin adsorption experiment was performed on activated carbon samples in the following manner. A test solution was prepared by adding an aqueous solution of indoxyl sulfate (potassium salt, available from Sigma-Aldrich) adjusted to 5 mg/mL to bovine blood anti-coagulated by adding heparin (10 U/mL). 50 mg (Table 1) or 10 mg (Table 2) of activated carbon sample was weighed in a polypropylene (PP) round-bottomed tube having a capacity of 2.0 mL, 0.1 mL of physiological saline was added and mixed, then 0.9 mL of test solution was added, and the mixture was mixed by inversion (10 revolutions/minute) at room temperature using a tube rotator. After that (in 5, 30, 60 minutes), centrifugation was performed at 3000 g for 10 minutes using a centrifuge, and a supernatant was obtained as a post-treatment plasma sample. An indoxyl sulfate adsorption rate of the activated carbon sample was calculated using the acquired plasma sample after treatment. The adsorption rate calculation equation is indicated below. An indoxyl sulfate concentration in plasma was measured using liquid chromatography mass spectrometry.

$$\text{Indoxyl sulfate adsorption rate }(\%)=(C_0-C)/C_0\times 100$$

$C_0$: Initial concentration of indoxyl sulfate before treatment $C$: Residual concentration of indoxyl sulfate after treatment The initial concentration $C_0$ concentration of indoxyl sulfate before treatment was measured by adding 0.1 mL of physiological saline to a polypropylene (PP) round-bottom tube and mixing them, then adding 0.9 mL of the test solution, and immediately centrifuging at 3000 g for 10 minutes using a centrifuge to obtain a supernatant as a plasma sample before treatment. The indoxyl sulfate concentration in the bovine blood was 3.5 to 3.8 mg/dL.

The initial concentration and the residual concentration of the same sample were measured using a biochemical automatic analyzer (for example, "Unicel DxC600 Clinical System" available from Beckman Coulter, Inc.), and the albumin adsorption rate was calculated using the above adsorption rate calculation equation.

The initial adsorption speed of indoxyl sulfate was calculated by dividing the adsorbed amount of indoxyl sulfate after 5 minutes by the time (5 minutes).

[Adsorption Test 2 (Immersion Method)]

Adsorption experiments of indole-3-acetic acid, phenyl sulfate, p-cresylsulfate, and hippuric acid were carried out on activated carbon samples by the following method. A plasma sample after treatment was obtained by the same method as in the adsorption test 1 except that a 5-component mixed solution containing the above-mentioned 4 components was added instead of adding an aqueous indoxyl sulfate solution. The indoxyl sulfate adsorption rate was calculated by the same method as in the indoxyl sulfate using the acquired plasma sample after treatment.

[Adsorption Test 3 (Liquid Passing Method)]

A mini-module was prepared by filling a container having an inlet for inflowing a fluid and an outlet for outflowing the fluid (for example, "Mobicol polypropylene column" available from Mobitec) with 200 mg of activated carbon sample. A test solution was prepared by adding an aqueous solution of indoxyl sulfate (potassium salt, available from Sigma-Aldrich) adjusted to 5 mg/mL to bovine blood anticoagulated by adding heparin (10 U/mL). The test solution was passed through a mini-module using a peristaltic pump, the test solution flowing out from the outlet was collected after 30 minutes, centrifuged at 3000 g for 10 minutes using a centrifuge, and a supernatant was obtained as a plasma sample after treatment. The indoxyl sulfate adsorption rate was calculated by the same method as in the adsorption test 1 using the acquired plasma sample after treatment.

Preparation of Activated Carbon

Example 1

First, 70 kg of a petroleum pitch with a softening point of 205° C. and an H/C atom ratio of 0.65 and 30 kg of naphthalene were charged into a pressure-resistant container with an internal volume of 300 liters and having a stirring blade and an outlet nozzle, and after the substances were melted and mixed while heating at 190° C., the mixture was cooled to from 80 to 90° C. The inside of the pressure-resistant container was pressurized by nitrogen gas, and the content was extruded from the outlet nozzle to obtain a string-shaped compact with a diameter of approximately 500 μm. Next, this string-shaped compact was pulverized so that the ratio (L/D) of the length (L) to the diameter (D) was approximately 1.5, and the resulting pulverized product was added to an aqueous solution in which 0.53 mass % of polyvinyl alcohol (degree of saponification: 88%) heated to 93° C. is dissolved, dispersed while agitating, and cooled to obtain a spherical pitch compact slurry. After the majority of the water was removed by filtration, the naphthalene in the pitch molded bodies was extracted and removed with n-hexane in a quantity of 6 times the mass of the spherical pitch molded bodies. Using a fluidized bed, the porous spherical pitch obtained in this manner was heated to 260° C. and held for 2 hour at 260° C. while hot air was passed through to oxidize, thereby producing heat-infusible porous spherical oxidized pitch.

Then, 100 g of the porous spherical oxidized pitch was placed in a vertical tube furnace 50 mm in diameter, and heated to 850° C. at a heating rate of 200° C./h under nitrogen gas flow. It was held at 850° C. for 1 hour to perform pre-heating, and a carbon precursor was obtained. Next, the obtained carbon precursor was subjected to an activation treatment at 850° C. in a nitrogen gas containing 50 vol % of steam until the bulk density was 0.46 g/cm³ so as to obtain spherical activated carbon 1.

Example 2

Using a fluidized bed, the porous spherical pitch obtained in this manner as Example 1 was heated to 240° C. and held for 2 hour at 240° C. while hot air was passed through to oxidize, thereby producing heat-infusible porous spherical oxidized pitch. Then, 40 g of the porous spherical oxidized pitch was placed in a tube furnace, and heated to 1350° C. at a heating rate of 250° C./h under nitrogen gas flow. It was held at 1350° C. for 4 hour to perform pre-heating, and a carbon precursor was obtained. Next, the obtained carbon precursor was subjected to activation treatment at 900° C. in a nitrogen gas containing 50 vol % of steam until the bulk density was 0.47 g/cm³ so as to obtain spherical activated carbon 2.

Example 3

Spherical activated carbon 3 was obtained in the same method as in Example 1 except that the activation treatment was performed until the bulk density was 0.60 g/cm³.

Example 4

Using a fluidized bed, the porous spherical pitch obtained in this manner as Example 1 was heated to 210° C. and held for 2 hour at 210° C. while hot air was passed through to oxidize, thereby producing heat-infusible porous spherical oxidized pitch. 100 g of the porous spherical oxidized pitch was placed in a vertical tube furnace 50 mm in diameter, and heated to 850° C. at a heating rate of 200° C./h under nitrogen gas flow. It was held at 850° C. for 1 hour to perform pre-heating, and a carbon precursor was obtained. Next, the obtained carbon precursor was subjected to activation treatment at 850° C. in a nitrogen gas containing 50 vol % of steam until the bulk density was 0.60 g/cm³ so as to obtain spherical activated carbon 4.

Example 5

Then, 40 g of the porous spherical oxidized pitch, which is the same as in Example 4, was placed in a tube furnace, and heated to 1200° C. at a heating rate of 250° C./h under nitrogen gas flow. It was held at 1200° C. for 4 hour to perform pre-heating, and a carbon precursor was obtained. Next, the obtained carbon precursor was subjected to activation treatment at 900° C. in a nitrogen gas containing 50 vol % of steam until the bulk density was 0.45 g/cm³ so as to obtain spherical activated carbon 5.

Example 6

Spherical Shirasagi (available from Osaka Gas Chemical Co., Ltd.) was used as activated carbon. Note that, this activated carbon is not manufactured as one lump, but is finely powdery activated carbon granulated with a binder.

Comparative Example 1

Then, 40 g of the porous spherical oxidized pitch, which is the same as in Example 4, was placed in a tube furnace, and heated to 1350° C. at a heating rate of 250° C./h under nitrogen gas flow. It was held at 1350° C. for 4 hour to perform pre-heating, and a carbon precursor was obtained. Next, the obtained carbon precursor was subjected to activation treatment at 900° C. in a nitrogen gas containing 50 vol % of steam until the bulk density was 0.45 g/cm³ so as to obtain spherical activated carbon 6.

Comparative Example 2

Spherical activated carbon 7 was obtained in the same method as in Example 1 except that the activation treatment was performed until the bulk density was 0.84 g/cm³.

Example 7

A petroleum pitch and $SiO_2$ were mixed homogeneously with each other in a weight ratio of 25:75, stirred at 300° C. with heating, and then cooled to room temperature to prepare a composite pitch material in which $SiO_2$ was dispersed. The obtained composite pitch was roughly pulverized by a hammer mill and then pulverized by a jet mill (Hosokawa Micron Corporation/100-AFG) to obtain a finely pulverized composite pitch. Next, the finely pulverized composite pitch was heated to 260° C. in an air atmosphere and held at 260° C. for 1 hour to carry out an infusibilization treatment. The obtained infusible finely ground composite pitch was held at 650° C. for 1 hour, and then treated with an aqueous solution of hydrofluoric acid to remove $SiO_2$, and thereby a porous carbon material was obtained. After placing 30 g of this porous carbon material in a crucible and holding it at 850° C. for 1 hour under nitrogen gas flow in a vertical tubular furnace, in nitrogen gas containing 50 vol % of steam, the activation treatment was carried out at 850° C. until the bulk density was 0.16 g/cm³, and thereby powdery activated carbon 1 was obtained.

Example 8

Powdery activated carbon 2 was obtained in the same method as in Example 7 except that the activation treatment was performed until the bulk density was 0.20 g/cm³.

Example 9

30 g of a phenol resin (Asahi Yukizai Corporation: BEAPS) was put in a crucible and held in a vertical tubular furnace under nitrogen gas flow at 850° C. for 1 hour to carry out preliminary heating to obtain a carbon precursor. Next, the obtained carbon precursor was subjected to activation treatment at 850° C. in a nitrogen gas containing 50 vol % of steam until the bulk density was 0.51 g/cm³ so as to obtain spherical activated carbon 8.

Example 10

Activated carbon fiber (Soen) was used in place of the spherical activated carbon.

Example 11

220 g of deionized-exchanged water and 58 g of methylcellulose were put in a 1 L separable flask, and 105 g of styrene, 184 g of 57% divinylbenzene (57% divinylbenzene and 43% ethylvinylbenzene), 2,2'-azobis (1.68 g of 2,4-dimethylvaleronitrile), and 63 g of 1-butanol as a porogen were appropriately added to the flask. Then, the interior of the system was replaced with nitrogen gas, and this two-phase system was heated to 55° C. while stirring at 150 rpm, and then held in that state for 20 hours. The obtained resin was filtered, dried with a rotary evaporator, and 1-butanol was removed from the resin by evaporation by vacuum-drying. The resulting resin was vacuum-dried for 12 hours at 90° C., to produce spherical porous synthetic resin having an average particle size of 180 μm. The obtained 100 g of spherical porous synthetic resin was put in a reaction tube with a grating, and infusibility treatment was performed in a vertical tube furnace. As the infusibility conditions, dry air was made to flow from bottom to top of the reaction tube at 3 L/min, heated to 260° C. at 5° C./h, and then held at 260° C. for 4 hours to obtain a spherical porous oxide resin. After the spherical porous oxide resin was heat-treated in a nitrogen atmosphere at 600° C. for 1 hour, using a fluidized bed, an activation treatment was performed at 820° C. in a nitrogen gas atmosphere containing 64.5 vol % steam until the bulk density was 0.50 g/cm$^3$ so as to obtain spherical activated carbon 9.

Comparative Example 3

Powdery activated carbon 3 was obtained in the same method as in Example 7, except that the activation treatment was not performed.

<Results>

Figure 3:
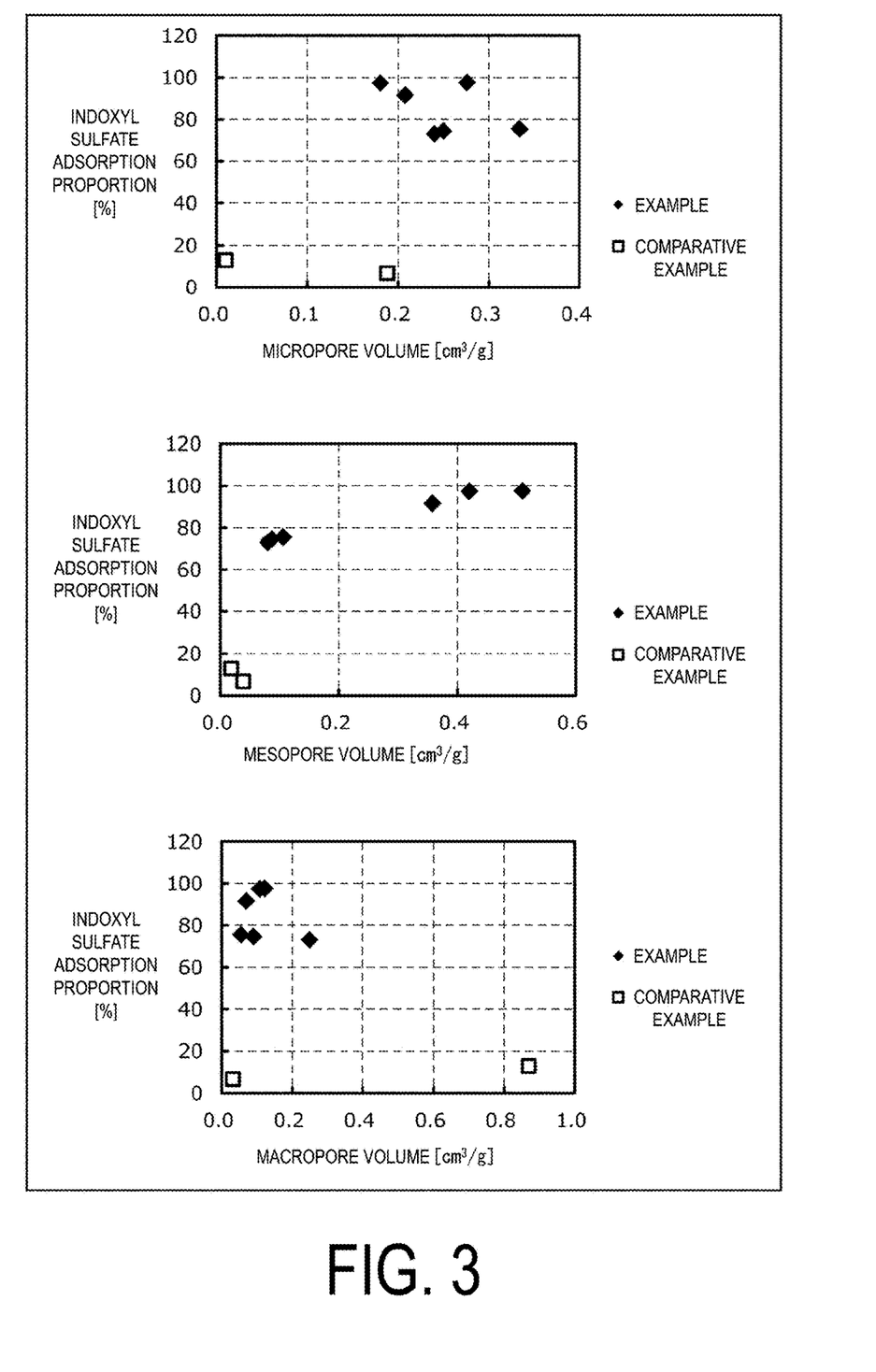
FIG. 3 is a graph illustrating results of examples of the present invention.

The results for indoxyl sulfate in each of the Examples and Comparative Examples are indicated in Tables 1 and 2 and FIG. 3. The indoxyl sulfate adsorption proportion in FIG. 3 is the value after 30 minutes.

TABLE 1

Table 1-1

| | Particle size [μm] | Bulk density [g/cm$^3$] | Crushing force [g/particle] | Crushing strength [kg/mm$^2$] | Specific surface area [m$^2$/g] | Micropore volume [cm$^3$/g] | Mesopore volume [cm$^3$/g] | Macropore volume [cm$^3$/g] | Indoxyl sulfate adsorption proportion % |
|---|---|---|---|---|---|---|---|---|---|
| Example 1 | 500 | 0.46 | 454 | 6.9 | 1913 | 0.21 | 0.36 | 0.07 | 92 |
| Example 2 | 500 | 0.47 | 276 | 4.2 | 1370 | 0.28 | 0.51 | 0.12 | 98 |
| Example 3 | 500 | 0.60 | 838 | 12.8 | 1239 | 0.33 | 0.11 | 0.06 | 76 |
| Example 4 | 500 | 0.60 | 774 | 11.8 | 924 | 0.25 | 0.09 | 0.09 | 75 |
| Example 5 | 500 | 0.45 | 280 | 4.3 | 664 | 0.18 | 0.42 | 0.11 | 97 |
| Example 6 | 1500 | 0.51 | 541 | 0.3 | 770 | 0.24 | 0.08 | 0.25 | 73 |
| Comparative Example 1 | 500 | 0.45 | 92 | 1.4 | 9.9 | 0.01 | 0.02 | 0.87 | 13 |
| Comparative Example 2 | 500 | 0.84 | 1487 | 22.7 | 476 | 0.19 | 0.04 | 0.03 | 7 |

Table 1-2

| | Albumin adsorption proportion After 60 minutes % | Amount of fine powders generated (ppm) | Pressure loss (MPa) | Macropore surface area [m$^2$/g] | Indoxyl sulfate adsorption proportion % | Initial adsorption speed of indoxyl sulfate [μg/min] |
|---|---|---|---|---|---|---|
| Example 1 | 0 | 222 | 0.019 | 0.33 | 8 | 0.6 |
| Example 2 | 0 | 265 | 0.017 | | | |
| Example 3 | 0 | 123 | 0.019 | | | |
| Example 4 | 0 | 135 | 0.018 | | | |
| Example 5 | 0 | 270 | | | | |
| Example 6 | 0 | 2340 | | | | |
| Comparative Example 1 | 0 | 1202 | | | | |
| Comparative Example 2 | 0 | 78 | 0.02 | | | |

TABLE 2

Table 2-1

| | Particle size [μm] | Bulk density [g/cm$^3$] | Specific surface area [m$^2$/g] | Micropore volume [cm$^3$/g] | Mesopore volume [cm$^3$/g] | Macropore surface area [m$^2$/g] | Indoxyl sulfate adsorption proportion % |
|---|---|---|---|---|---|---|---|
| Example 7 | 2.7 | 0.16 | 472 | 0.15 | 0.17 | 29.2 | 95 |
| Example 8 | 2.9 | 0.20 | 168 | 0.10 | 0.10 | 28.2 | 50 |
| Example 9 | 8.7 | 0.51 | 1560 | 0.58 | 0.13 | 5.3 | 98 |
| Example 10 | — | 0.04 | 1200 | 0.29 | 0.24 | 0.80 | 31 |
| Example 11 | 111 | 0.50 | 1763 | 0.23 | 0.32 | 0.46 | 51 |
| Comparative Example 3 | 5.2 | 0.23 | 42 | 0.02 | 0.050 | 27.6 | 2 |

TABLE 2-continued

Table 2-2

|  | Indoxyl sulfate adsorption proportion % | Initial adsorption speed of indoxyl sulfate [μg/min] | Albumin adsorption proportion After 60 minutes % | Pressure loss (MPa) |
|---|---|---|---|---|
| Example 7 | 99 | 7.2 | 0 | Not determined |
| Example 8 | 60 | 3.8 | 0 | Not determined |
| Example 9 | 100 | 7.4 | 0 | Not determined |
| Example 10 | 60 | 2.3 | 0 |  |
| Example 11 | 83 | 3.9 | 0 |  |
| Comparative Example 3 | 3 | 0.1 | 0 | Not determined |

As indicated in Tables 1 and 2 and FIG. 3, it was found that the adsorption proportion of indoxyl sulfate was not correlated with the micropore volume and the macropore volume, but was highly correlated with the mesopore volume. In addition, in each of the Examples, the adsorption proportion increased and approached 100% as time passed. On the other hand, in the comparative example, the adsorption proportion hardly increased and remained low even after a lapse of time. In addition, in each of the Examples and Comparative Examples, albumin was not adsorbed at all.

Further, when comparing Example 3 with Example 8 of which the mesopore volumes were close, it was found that Example 8 having a larger macropore surface area had a higher adsorption speed (initial adsorption speed).

The results for indole-3-acetic acid, phenylsulfate, p-cresylsulfate, and hippuric acid are indicated in Table 3. Here, as a representative, the results of Example 5, Example 11, Comparative Example 1, and Comparative Example 2 after 30 minutes are indicated.

TABLE 3

|  | adsorption proportion After 30 minutes % | | | | |
|---|---|---|---|---|---|
|  | Indoxyl sulfate | Indole-3-acetic acid | Phenyl-sulfate | p-cresyl sulfate | Hippuric acid |
| Example 5 | 97 | 98 | 98 | 93 | 100 |
| Example 11 | 100 | 100 | 100 | 99 | 100 |
| Comparative Example 1 | 13 | 0 | 0 | 0 | 7 |
| Comparative Example 2 | 7 | 0 | 1 | 0 | 2 |

As is clear from Table 3, indole-3-acetic acid, phenylsulfate, p-cresylsulfate, and hippuric acid also showed the same level of adsorption as indoxyl sulfate. Note that, in other Examples and Comparative Examples, the same results as in the case of indoxyl sulfate were obtained. In addition, the albumin adsorption proportion was 0% in an experiment using indole-3-acetic acid, phenylsulfate, p-cresylsulfate, and hippuric acid.

Further, the results obtained by the liquid passing method are indicated in Table 4. Here, as a representative, the results of Example 1 after 30 minutes are indicated.

TABLE 4

|  | Evaluation method | Indoxyl sulfate % |
|---|---|---|
| Example 1 | Immersion method | 92 |
|  | Liquid passing method | 87 |

As is apparent from Table 4, even in the case of the liquid passing method, a good adsorption proportion of indoxyl sulfate was shown as in the immersion method. In addition, the adsorption proportion increased and approached 100% as time passed. In addition, also in the other Examples and Comparative Examples, the same results as in the immersion method were obtained in the case of the liquid passing method. In addition, the albumin adsorption proportion was 0% even by the liquid passing method.

INDUSTRIAL APPLICABILITY

The present invention can be used for hemodialysis and the like.

REFERENCE SIGNS LIST

1 Toxin separator
1a Blood inlet
1b Blood outlet
2 Activated carbon
3 Dialyzer
3a Blood inlet
3b Blood outlet
3c Dialysate inlet
3d Dialysate outlet
11 Tube
12 Pump
13 Tube
14 Tube
15 Tube
16 Dialysate supply unit
17 Tube
18 Tube
100 Blood purification system

The invention claimed is:
1. A toxin separator that separates toxin from a biological fluid, wherein the toxin is bound to protein to be present in the biological fluid, the toxin separator includes activated carbon having a pore volume of pores having a pore diameter from 1.4 to 35 nm, as measured by a nitrogen adsorption method, of 0.06 cm$^3$/g or greater, and the activated carbon has a pore surface area of 0.10 m$^2$/g or greater of pores having a pore diameter from 50 to 10000 nm as measured by a mercury intrusion porosimetry.

2. The toxin separator according to claim 1, wherein the toxin is a uremic toxin.

3. The toxin separator according to claim 1, wherein the activated carbon is spherical.

4. The toxin separator according to claim 1, wherein the biological fluid is blood.

5. The toxin separator according to claim 1, which is a blood purification column.

6. A blood purification system comprising:
the toxin separator described in claim 1; and
a dialyzer.

7. A toxin separation method of separating toxin from a biological fluid,
wherein the toxin is bound to protein to be present in the biological fluid, and
the method includes passing the biological fluid through the toxin separator described in claim 1.

* * * * *